(12) United States Patent
Parry et al.

(10) Patent No.: US 10,473,501 B2
(45) Date of Patent: Nov. 12, 2019

(54) MULTIPHASE VORTEX FLOW METER

(71) Applicant: SCHLUMBERGER TECHNOLOGY CORPORATION, Sugar Land, TX (US)

(72) Inventors: Andrew Parry, Clamart (FR); Yann Dufour, Clamart (FR)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 0 days.

(21) Appl. No.: 15/802,491

(22) Filed: Nov. 3, 2017

(65) Prior Publication Data

US 2018/0172495 A1 Jun. 21, 2018

(30) Foreign Application Priority Data

Dec. 16, 2016 (EP) .................................. 16290239

(51) Int. Cl.
*G01F 1/66* (2006.01)
*G01F 1/44* (2006.01)
(Continued)

(52) U.S. Cl.
CPC ................ *G01F 1/74* (2013.01); *E21B 47/10* (2013.01); *G01F 1/32* (2013.01); *G01F 1/3245* (2013.01); *G01F 1/34* (2013.01); *G01F 1/7082* (2013.01); *G01F 1/712* (2013.01); *G01F 5/00* (2013.01); *G01F 7/00* (2013.01); *G01N 9/32* (2013.01); *G01N 33/2847* (2013.01); *G01F 1/3254* (2013.01); *G01F 1/3272* (2013.01); *G01F 1/3281* (2013.01)

(58) Field of Classification Search
CPC ..................................... G01F 1/66; G01F 1/44
See application file for complete search history.

(56) References Cited

U.S. PATENT DOCUMENTS

| | | | |
|---|---|---|---|
| 6,575,043 B1 | 6/2003 | Huang et al. | |
| 8,346,491 B2 * | 1/2013 | Loose | G01F 1/666 324/306 |

(Continued)

FOREIGN PATENT DOCUMENTS

CN 101699225 A 4/2010

OTHER PUBLICATIONS

Hulin, J-P. et al, "Experimental Study of Vortex Emission Behind Bluff Obstacles in Gas Liquid Vertical Two-Phase Flow", International Journal of Multiphase Flow, 1982, 8(5), pp. 475-490.

(Continued)

*Primary Examiner* — Jewel V Dowtin

(57) ABSTRACT

A multiphase flowmeter for detection of fluid flow by monitoring of vortex frequency or perturbation time of flight. The flowmeter includes a bluff body to facilitate formation of vortices during a consistent phase of a flowing fluid. Thus, monitoring frequency of the vortices may be employed to ascertain flowrate. Further, the bluff body may also facilitate formation of perturbations during transitioning phase of the fluid and include perturbation sensors at multiple known locations along the flow-path. Thus, analysis of perturbation detection times at the different locations may be used to ascertain flowrate even in the absence of vortices.

20 Claims, 5 Drawing Sheets

(51) Int. Cl.
*G01F 1/74* (2006.01)
*G01F 1/32* (2006.01)
*E21B 47/10* (2012.01)
*G01N 9/32* (2006.01)
*G01N 33/28* (2006.01)
*G01F 1/34* (2006.01)
*G01F 1/708* (2006.01)
*G01F 1/712* (2006.01)
*G01F 5/00* (2006.01)
*G01F 7/00* (2006.01)

(56) References Cited

U.S. PATENT DOCUMENTS 8,683,874 B2 * 4/2014 Limacher .............. G01F 1/3218 73/861.24
10,175,089 B2 * 1/2019 Schmid ............... G01F 25/0007
2015/0276445 A1 10/2015 Black et al.
2017/0030748 A1 * 2/2017 Sapack .................... G01F 1/66
2018/0143048 A1 * 5/2018 Lewis ...................... G01F 1/34

OTHER PUBLICATIONS

Coulthard, J. et al., "Vortex wake transit time measurements for flow metering", Flow Measurement and Instrumentation, 1993 vol. 4(4), pp. 269-272.

Coulthard, J. et al., "Comparisons of different bluff bodies in vortex wake transit time measurements", Flow Measurement and Instrumentation, 1993, 4(4), pp. 273-275.

Menz, B., "Vortex flowmeter with enhanced accuracy and reliability by means of senson fusion and self-validation", Measurement, 1977, 22, pp. 123-128.

Wang, H. et al., "A remote measuring flow meter for petroleum and other industrial applications", Measurement Science and Technology, 1998, 9(5), pp. 779-789.

* cited by examiner

MULTIPHASE VORTEX FLOW METER

CROSS-REFERENCE TO RELATED APPLICATIONS

This application claims benefit of European patent application serial number 16290239.9, filed Dec. 16, 2016 and titled MULTIPHASE VORTEX FLOW METER, the entire disclosure of which is herein incorporated by reference.

BACKGROUND

Field

The present disclosure relates to techniques for measuring multiphase flows in wellbores. More particularly, the present disclosure relates to tools and methods for intelligent completions and monitoring systems, including monitoring multiphase fluid flow in wellbores.

Description of the Related Art

Exploring, drilling and completing hydrocarbon and other wells are generally complicated, time consuming and ultimately very expensive endeavors. In recognition of the potentially enormous expense of well completion, added emphasis has been placed on well monitoring and maintenance throughout the life of the well. Increasing the life and productivity of a given well may help ensure that the well provides a healthy return on the significant investment involved in its completion. Thus, over the years, well diagnostics and treatment have become more sophisticated and critical facets of managing well operations.

In certain circumstances, well diagnostics takes place on a near-continuous basis such as where pressure, temperature or other sensors are disposed downhole, for example, in conjunction with production tubing. A monitoring tool with sensors may be affixed downhole with tubing in order to track well conditions during hydrocarbon recovery. In some cases, the monitoring tools may be fairly sophisticated with capacity to simultaneously track a host of well conditions in real time. Thus, both sudden production profile changes and more gradual production changes over time may be accurately monitored. Such monitoring allows for informed interventions or other adjustments where appropriate. By the same token, these types of conditions may be monitored in conjunction with an intervention such as a logging application as opposed to relying on permanently installed downhole components.

Whether permanently installed or introduced with other interventional equipment, monitoring tools may be equipped with flowmeters in order to keep track of downhole fluid flow. For example, monitoring of downhole fluid flow may be a fairly direct indicator of the hydrocarbon recovery rate for a given well. The flowmeter itself is often a Venturi flowmeter which introduces a bottleneck-type of restriction to the flow of fluid resulting in measurable differential pressure data. This data may be used to ascertain fluid flowrate and to indirectly estimate density.

Unfortunately, there are certain limitations to using Venturi flowmeters to ascertain flowrate in a well. For example, the flowrate is not directly measured. Instead, it is estimated based on the relationship between the pressure drop induced by a constriction and the product of density and the square of the volumetric flowrate. As a result, the computation introduces a certain degree of inherent inaccuracy because of a direct measurement, a pressure drop from differential pressure measurements is correlated to the square of flowrate. Thus, even a minor inaccuracy in a pressure measurement may be amplified when translated to flowrate. Once more, the range of flowrate detectable by such a flowmeter is also limited due to the indirect nature of the meter. The need to correlate pressure to a square of the flowrate means that the flowrate needs to be within a manageable window in order to ensure practical correlation to detected pressure.

In light of the limitations on venturi flowmeters, vortex flowmeters are often utilized. A vortex flowmeter is capable of taking more direct measurements of flowrate through inducing and monitoring vortices. More specifically, instead of introducing a restriction or bottlenecking type of feature to a flow of fluid, a vortex flowmeter introduces a bluff body to a flow of fluid. A bluff body is an elongated structure that traverses a flow of fluid in a channel and is of a shape that is configured to encourage the formation of vortices. As the flow meets a generally flat surface face of the stationary bluff body, vortices of swirling fluid will form in a regular pattern and continue on downstream for a period, eventually attenuating. This regular pattern of vortices will take place at a frequency that is directly related to the flowrate of the flowing fluid. As a result, sensors positioned immediately adjacent and downstream of the face of the bluff body to detect the frequency of the forming vortices may provide flowrate information. Acoustic sensors, pressure sensors, and other sensors may be used to acquire such vortex frequency information.

Because the vortex flowmeter provides a more direct measurement of flowrate, accuracy may be improved. Similarly, the direct measurement also means that the range of detections is not limited based on the need to keep values within a practical window for sake of calculations. Thus, in theory, a vortex flowmeter may provide greater accuracy and range than a Venturi flowmeter.

Unfortunately, the vortex flowmeter is not able to provide usable detections where the fluid type changes from one type to another. For example, it is not uncommon in a well for a hydrocarbon liquid to transition to a gas or for water to emerge in the fluid stream. When this type of phase change occurs, the uniform vortices are interrupted by perturbations that are not detectable in an understandable manner by the sensors at the bluff body and instead of detecting flowrate, no detection at all may occur even where the flowrate has not changed. Thus, as a practical matter, operators are often left with only the option of utilizing a less accurate, narrower range flowrate detector as opposed to risking no detection at all.

SUMMARY

A method of detecting flowrate in a fluid channel is disclosed. The method includes introducing a bluff body to a flow of fluid in the channel in order to form shedded vortices. A perturbation in the vortices due to phase change in the flow of fluid may take place which is detected at a first location and then again detected at a second location downstream of the first location. Thus, a flowrate of the perturbation may be calculated based on a time difference between the detections. A flowrate of a vortex of the shedded vortices may also be calculated in this manner. Further, a flowmeter with a housing defining the channel may be provided and which also accommodated the bluff body. Therefore, sensors at the two locations may be utilized to ascertain time of flight information for the detecting of the flowrate.

However, many modifications are possible without materially departing from the teachings of this disclosure.

Accordingly, such modifications are intended to be included within the scope of this disclosure as defined in the claims.

BRIEF DESCRIPTION OF THE DRAWINGS

So that the manner in which the above recited features can be understood in detail, a more particular description may be had by reference to embodiments, some of which are illustrated in the appended drawings, wherein like reference numerals denote like elements. It is to be noted, however, that the appended drawings illustrate various embodiments and are therefore not to be considered limiting of its scope, and may admit to other equally effective embodiments.

Certain embodiments of the disclosure will hereafter be described with reference to the accompanying drawings, wherein like reference numerals denote like elements. It should be understood, however, that the accompanying figures illustrate the various implementations described herein and are not meant to limit the scope of various technologies described herein, and.

DETAILED DESCRIPTION

In the following description, numerous details are set forth to provide an understanding of some embodiments of the present disclosure. However, it will be understood by those of ordinary skill in the art that the system and/or methodology may be practiced without these details and that numerous variations or modifications from the described embodiments may be possible.

In the specification and appended claims: the terms "connect", "connection", "connected", "in connection with", and "connecting" are used to mean "in direct connection with" or "in connection with via one or more elements"; and the term "set" is used to mean "one element" or "more than one element". Further, the terms "couple", "coupling", "coupled", "coupled together", and "coupled with" are used to mean "directly coupled together" or "coupled together via one or more elements". As used herein, the terms "up" and "down", "upper" and "lower", "upwardly" and downwardly", "upstream" and "downstream"; "above" and "below"; and other like terms indicating relative positions above or below a given point or element are used in this description to more clearly describe some embodiments of the disclosure.

In the following description, numerous details are set forth to provide an understanding of the present disclosure.

However, it will be understood by those skilled in the art that the embodiments described may be practiced without these particular details. Further, numerous variations or modifications may be employed which remain contemplated by the embodiments as specifically described.

Embodiments are described with reference to certain types of downhole hydrocarbon recovery operations. In particular, focus is drawn to flowmeters and techniques applied to permanent installations for long term flow monitoring in a well. However, tools and techniques detailed herein may be employed in a variety of other manners. For example, embodiments of multiphase flowmeters as detailed herein may be configured for use with interventional equipment such as logging tools. Indeed, such flowmeters may even be employed outside of the oilfield environment. Regardless, so long as perturbations are detected at multiple locations to allow for the calculation of fluid transit time even in the absence of clear vortex frequency, appreciable benefit may be realized.

Figure 1:
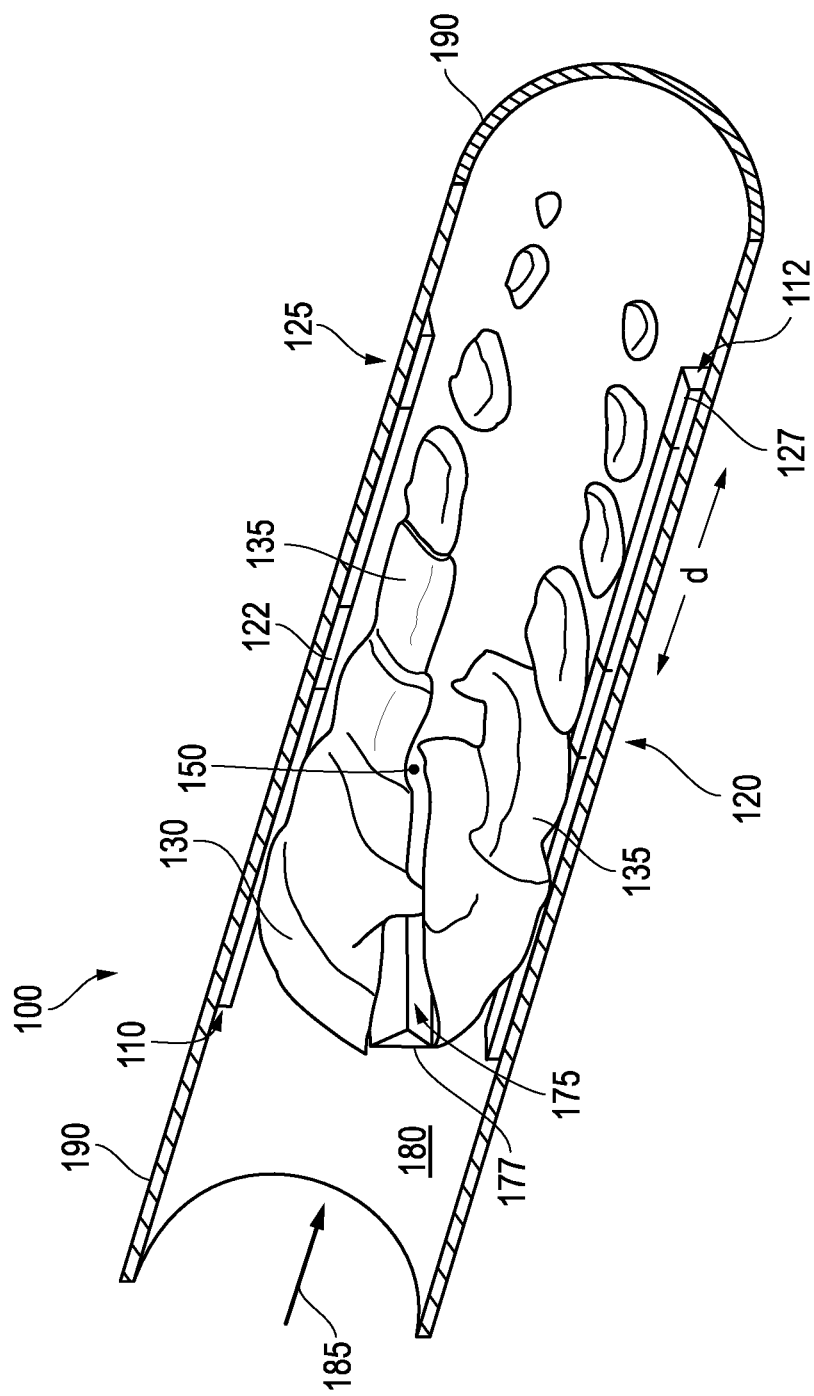
FIG. 1 is a side perspective view of an embodiment of a multiphase vortex flowmeter.

Referring now to FIG. 1, a side perspective cross-sectional view of an embodiment of a multiphase vortex flowmeter 100 is shown. In this view, a fluid 130 is shown passing through a channel 180 of the flowmeter 100 defined by a cylindrical housing 190. The fluid 130 is flowing in a direction indicated by an arrow 185 and intersects a bluff body 175 at a face 177 thereof. In this manner, discrete vortices 135 may emerge at a detectable frequency. More specifically, with brief added reference to FIG. 3A for added illustration, the frequency of the emergence of these vortices may be detected by one or more differential pressure sensors 150, 350 to ascertain a rate of flow for the fluid 130. The higher the frequency/rate of vortex formation, the faster the flow.

Continuing with reference to FIG. 1, the flowmeter 100 is also outfitted with more downstream supplemental sensor assemblies 110, 112. In addition to the bluff body vortex frequency sensors (e.g. 150), assemblies 110, 112 may be provided to help ascertain a flowrate of the fluid 130 when vortex formation is compromised. For example, as detailed further below, as a fluid 130 changes phases, such as from a predominantly liquid oil to a hydrocarbon gas or water, it may fail to present discernable vortices 135. Instead, with added reference to FIGS. 3B and 3C, more random disturbances or perturbations 230 may emerge for a period of time. These perturbations may emerge in response to fluid encountering the bluff body 175 but may occur at no particularly reliable frequency from which to ascertain flow rate from a single sensor location at the bluff body 175. In these circumstances, the supplemental sensor assemblies 110, 112, which continue more downstream, are provided so as to prevent any substantial interruption in the acquisition of flowrate information. Of course, these sensor assemblies 110, 112 are referred to as 'supplemental' in the embodiment shown. However, in other embodiments, these assemblies 110, 112 may be primary in nature, providing flow information from vortex detections 135 as well, perhaps in complete absence of the sensors right at the bluff body 175 (e.g. 150).

In the embodiment of FIG. 1, the supplemental sensor assemblies 110, 112, include two separate detection locations or zones 120, 125 that are spaced apart by a known distance (d). For example, in this embodiment, the flowmeter 100 may be no more than a few inches in length with the distance (d) being less than one inch. Regardless, sensors 122, 127 capable of detecting a perturbation 230 are positioned at each zone 120, 125 (see FIGS. 3B and 3C). Such sensors 122, 127 may be temperature sensors, pressure sensors, acoustic sensors, ultrasonic, piezo-patches or others, likely operable at up to several hundred Hertz and capable of detecting a fluid characteristic of a perturbation 230 (and/or a vortex 135). Thus, when substantially the same characteristic is detected at a first sensor 122 and then a second sensor 127 at a known distance (d) from the first, a time of flight calculation may be utilized to ascertain flowrate. As a practical matter, as indicated above, this means that in spite of the change in phase of a flowing fluid and a consequent absence of a discernable vortex frequency, flowrate may continue to be determined.

Figure 2:
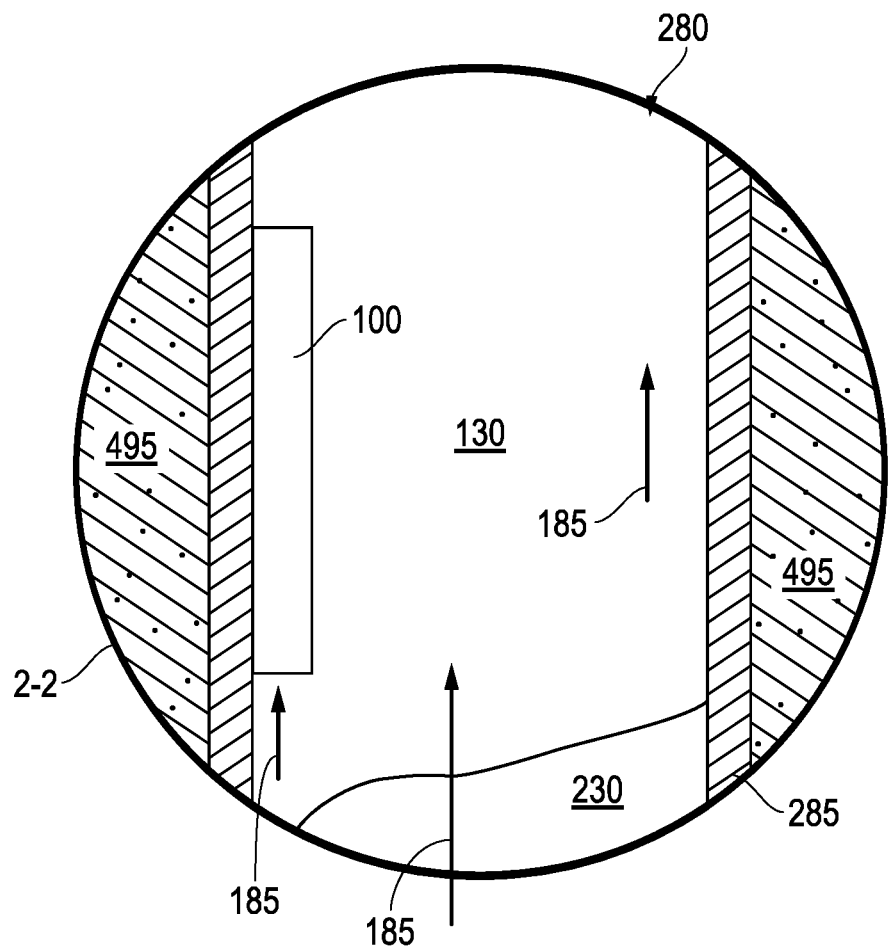
FIG. 2 is an enlarged view of a section of a well taken from 2-2 of FIG. 4 and accommodating the flowmeter of FIG. 1.
Figure 4:
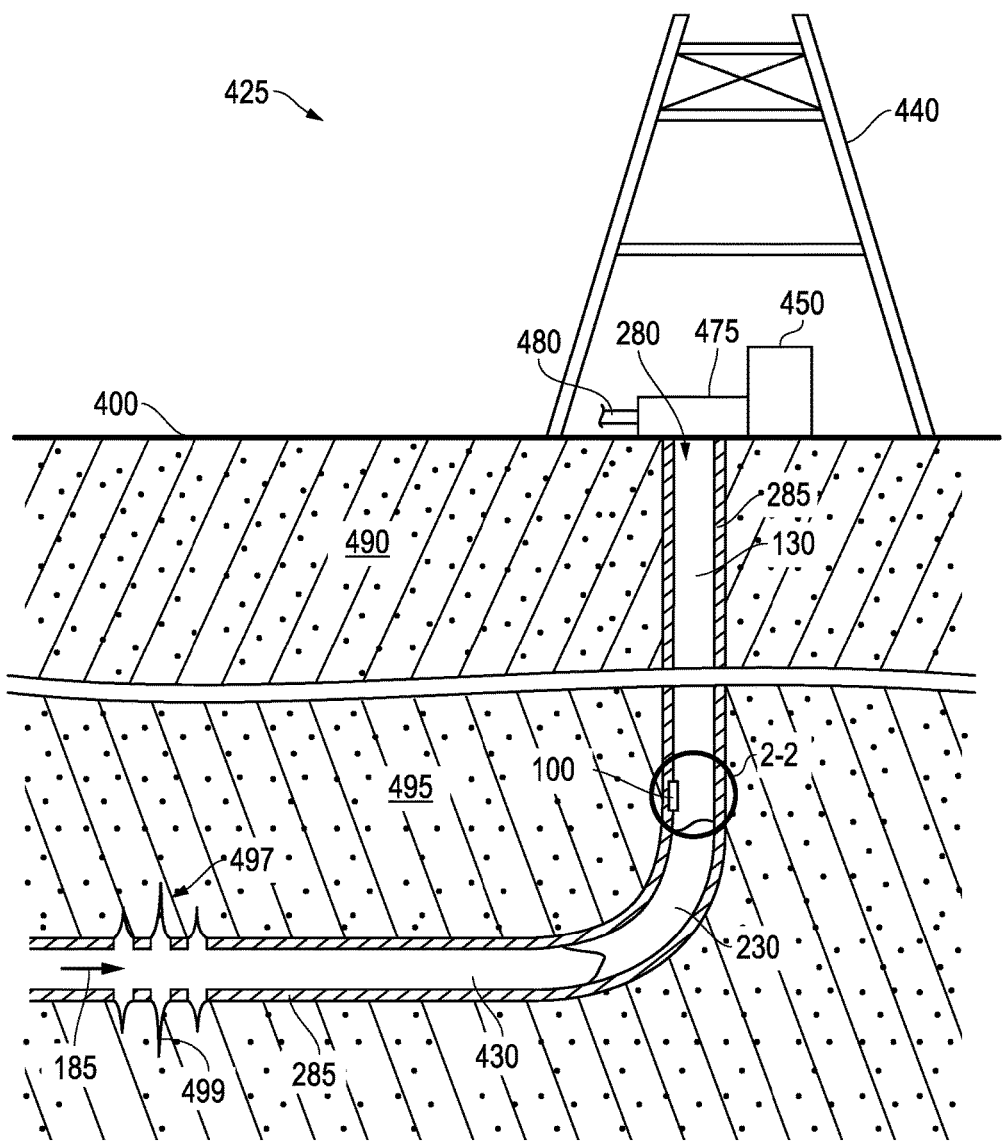
FIG. 4 is an overview depiction of an oilfield accommodating a well with the flowmeter of FIG. 2 therein for measuring fluid flow in the well even during phase change.

Referring now to FIG. 2, an enlarged view of a section of a well 280 taken from 2-2 of FIG. 4 is shown. In this view, the flowmeter 100 of FIG. 1 can be seen accommodated within the well 280. More specifically, the flowmeter 100 is shown secured to a casing 285 defining the well 280 as it traverses a formation 495. In this way, the flowmeter 100 may be utilized to ascertain fluid flow (see arrows 185). Indeed, as detailed further below, even as the fluid changes from one phase (130) to another (230), flowrate detections may continue in an uninterrupted fashion as alluded to above.

Figure 3A:
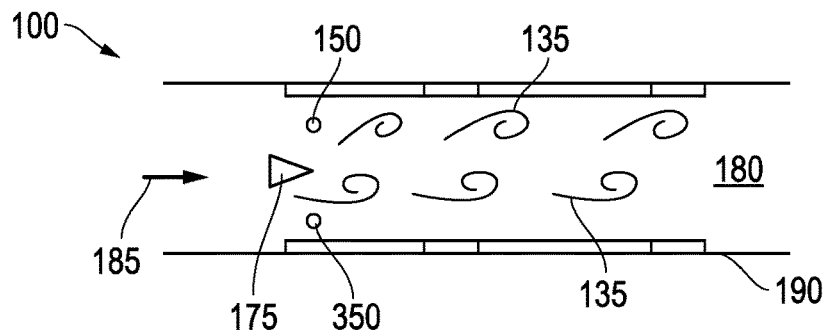
FIG. 3A is a side cross-sectional view of the flowmeter of FIG. 1 showing the emergence of vortices as indicative of flowrate.
Figure 3B:
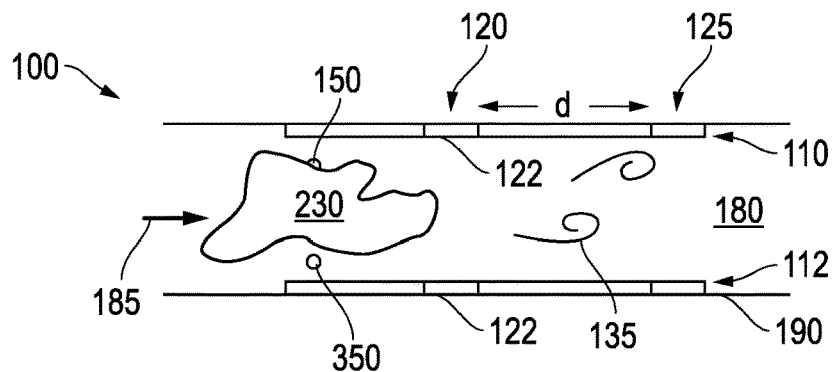
FIG. 3B is a side cross-sectional view of the flowmeter of FIG. 3A as the vortices transition into a perturbation during a fluid phase change.
Figure 3C:
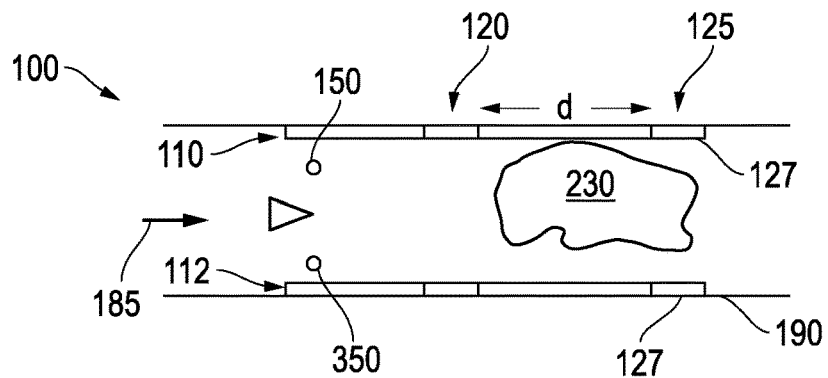
FIG. 3C is a side cross-sectional view of the flowmeter of FIG. 3B as the perturbation of flowing fluid traverses a known distance.

Referring now to FIGS. 3A-3C, side cross-sectional schematic views of the flowmeter 100 of FIG. 1 are shown as fluid vortices 135 give way to disruptive perturbations 230 as phase changes occur. With added reference to FIG. 4, as fluid flow 185 continues through the channel 180, a period of transition from one fluid type to another may occur such as liquid hydrocarbons (130) giving way to a mixture (230) with hydrocarbon gas and eventually gas alone (430). Nevertheless, as detailed herein, uninterrupted flowrate measurements may continue in spite of the phase change and perturbations (e.g. 230).

With specific reference to FIG. 3A, vortices 135 are shown that may present at a detectable frequency that is indicative of flowrate. As noted above, this is to be expected where the fluid flowing through the channel 180 is of a consistent phase, such as where a particular liquid is present without any substantial gas or other liquid type mixed therewith. Indeed, with such a uniform fluid present, pressure sensors 150, 350 at a single location adjacent the bluff body 175 may be sufficient to detect the frequency of the vortex formation so as to ascertain flowrate in a direct, linear fashion. As indicated, the sensors 150, 350 are located adjacent the bluff body 175 given that this is the source of vortex formation. Thus, a substantially direct and accurate measurement is available without concern over drift or other similar issues. However, the sensors 150, 350 may also be positioned at other locations within the housing 190 downstream of the bluff body 175. Indeed, along these lines, in the embodiment shown, the flowmeter 100 does include additional or "supplemental" sensing capacity to address circumstances when fluid flow continues but without a regular frequency presentation of vortices 135.

Referring now to FIG. 3B, the flowmeter 100 of FIG. 3A is depicted as the fluid type within the channel 180 begins to change. Thus, as suggested above, additional detection zones 120, 125 with supplemental sensors 122, 127 may come into play. For example, as the fluid type transitions to a mix of liquid and gas, the interaction of the fluid with the bluff body 175 of FIG. 3A may cease to present vortices 135 at discernable frequencies (see FIG. 3A). However, while not presenting at a discernable frequency, the interaction of the transitioning fluid with the bluff body 175 may result in the emergence of detectable perturbations 230.

As shown in FIG. 3B, the perturbation 230 may continue to flow (arrow 185) through the channel 180 bypassing an initial detection zone 120. In the embodiment shown, this zone 120 is provided by way of sensor assemblies 110, 112 equipped with sensors 122. While perturbations such as the one depicted (230) may not present at clear usable frequencies, individual characteristics of a given perturbation 230 may nevertheless be detectable. For example, the sensors 122 in the initial detection zone 120 may be piezo, acoustic, pressure, temperature or other type of sensors as noted above for detecting a characteristic of the perturbation 230. The availability of durable cost-effective piezo-patches, in particular, may make these types of sensors desirable. For example, an encapsulated, thin walled patch may be used to circumferentially line the housing 190 with openings or exposures provided in the area of a given zone 120 (or 125 as discussed below).

In one embodiment, a single sensor 122 may suffice for the zone 120. Additionally, in another embodiment, a sensor 122 is provided that is configured to work as an acoustic receiver for an acoustic signal that is transmitted from the opposite side of the channel 180 (e.g. at the location of the opposite sensor 122). In this scenario, the transmitted signal may be compared to the detection for ascertaining the presence of the perturbation 230 in the initial zone 120.

With specific reference now to FIG. 3C, a cross-sectional view of the flowmeter 100 of FIG. 3B is shown as the perturbation 230 detected within the initial zone 120 continues along with the flow (185) across a distance (d) and reaches the second zone 125. Again, while there is no particularly discernable frequency of perturbations, the same perturbation 230 may still be detected again within the second zone 125 via sensors 127. When this second set of sensors 127 detects a perturbation of substantially the same temperature, pressure or other characteristic that has been detected in the initial zone 120, the fact that this is the same perturbation 230 may be confirmed. Once more, "the time of flight" or the time it takes for the detected perturbation 230 to traverse the known distance (d), allows for the flowrate to be determined. Thus, as a practical matter, even in the absence of a discernable frequency of vortices 135 (see FIG. 3A), flowrate may continue to be ascertained.

While the embodiment of FIGS. 3A-3C illustrate vortex-focused sensors 150, 350 that are employed during periods where fluid is not changing phases, and supplemental sensors 122, 127 for periods of phase change as noted above, other embodiments are possible. For example, the vortex-focused sensors 150, 350 may be pressure sensors that are used to detect a frequency of vortices 135 when present but also utilized to detect pressure of a perturbation 230 in absence of vortices 135. In this embodiment, the sensors 150, 350 at the bluff body 175 may provide the initial zone of detection for the perturbation 230. When this is the case, another zone such as 120 (or 125), may be at a known distance from the bluff body sensors 150, 350 utilizing pressure sensors 122 (or 127) to make the second detection of the perturbation 230. Thus, a time of flight computation may again be made for sake of ascertaining flowrate. As a practical matter, this may reduce number of zones and sensors required to determine flowrate during a fluid transition from one phase to another.

In yet another embodiment, supplemental sensors 122, 127 at one zone 120 or another 125 may even be employed during periods of reliable vortex shedding where the frequency of vortices 135 is ascertained by sensors 150, 350. For example, flowrate detection of a consistent single phase fluid may take place as described above at FIG. 1. Further, at a known distance from the bluff body sensors 150, 350, supplemental sensors 122 (or 127) at a subsequent zone 120

(or 125) may still be employed to provide time of flight information in order to enhance the flowrate analysis under way.

Referring now to FIG. 4, the flowmeter 100 is shown in a real-world environment where it may be used to provide continuous flowrate information even as fluid there-through changes from one phase to another. Specifically, an overview depiction of an oilfield 400 is shown with a well 280 accommodating the flowmeter 100 of FIG. 2. At this downhole, permanently installed location, fluid flow in the well 280 may be measured on a substantially continuous basis regardless of phase change.

Continuing with reference to FIG. 4, the wellsite includes equipment 425 in the form of a rig 440 to support initial downhole completions or subsequent interventions. Further, a production line 480 emerges from a wellhead 475 for collection of downhole fluids 130, 230, 430. A control unit 450 adjacent the wellhead 475 may be utilized for a variety of purposes, including analysis of flowrate data from the flowmeter 100.

The well 280 is outfitted with a casing 285 traversing various formation layers 490, 495. A production region 497 with perforations 499 may be targeted for production. However, fluid may flow (see arrow 185) from locations downhole of this region 497 as well. Indeed, in the depicted overview, fluid in the well 280 includes hydrocarbon liquid 130 that gives way for a time to fluid gas 430, perhaps originating from outside of the targeted production region 497. Thus, phase change fluid 230 is present between the liquid 130 and gas 430. For illustrative purposes, this phase change fluid 230 is the same fluid that makes up the perturbation 230 as depicted in FIGS. 3B and 3C referenced above, thus, sharing the same feature numbering.

For the reasons elaborated above, in spite of the phase change, flowrate may be continuously determined as all fluid (130, 230, 430) makes its way up the well 280 and is produced at surface. Specifically, in the embodiment shown, flowrate information may be relayed to the control unit 450 where it is analyzed in an uninterrupted fashion regardless of fluid type or phase change conditions. Relaying of the detection information from the flowmeter 100 may be achieved wirelessly, through fiber optics, electrical line or by way of any practical conventional mode for the oilfield environment. Regardless, the information may be attained and analyzed on a substantially continuous basis irrespective of the multiphase nature of the fluids due to the unique features of the flowmeter 100.

Figure 5:
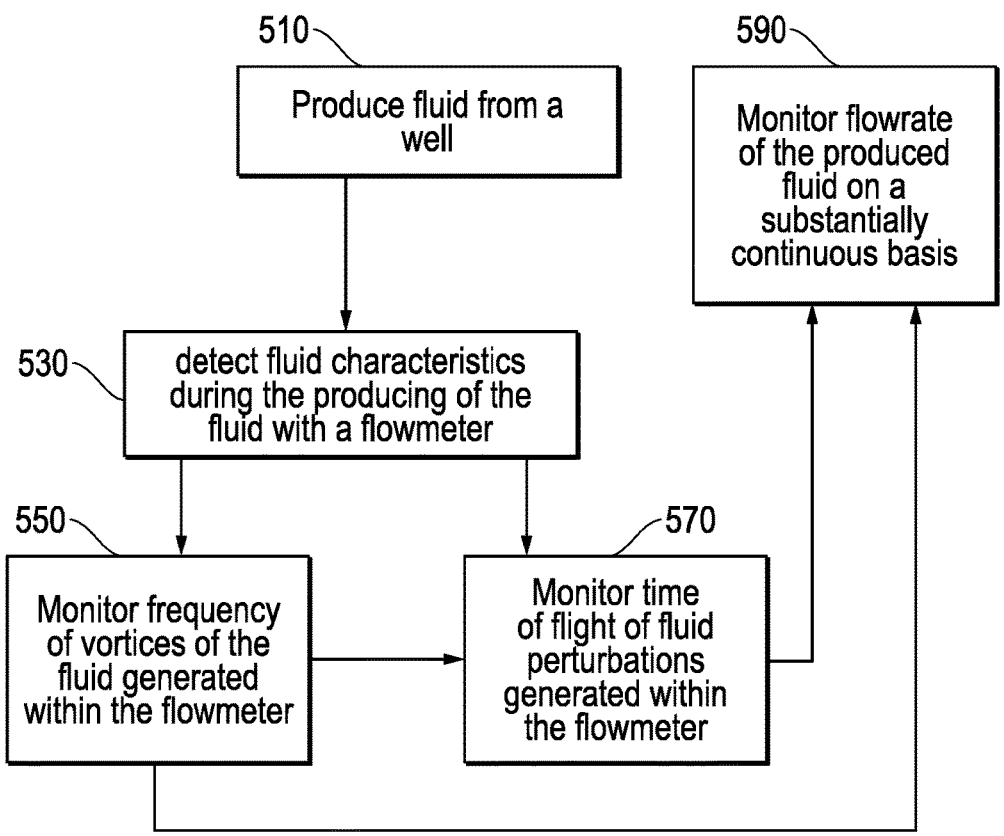
FIG. 5 is a flow-chart summarizing an embodiment of employing a multiphase flowmeter in a well during oilfield operations.

Referring now to FIG. 5, a flow-chart summarizing an embodiment of employing a multiphase flowmeter in a well during oilfield operations is depicted. Specifically, as indicated at 510 and 590, when fluid is produced in a well, flowrate may be monitored on a substantially continuous basis. This involves detecting with a flowmeter fluid characteristics as indicated at 530. When the fluid is in a single, consistent phase and type, this may include monitoring frequency of vortices generated within the flowmeter as indicated at 550. However, even when such detections are not available, such as during a transitional phase for the fluid, time of flight monitoring of perturbations may take place as noted at 570. In fact, in an embodiment, time of flight monitoring of generated vortices may also be utilized where the fluid is not in a transitional phase, either as a supplement to, or replacement for, vortex frequency detections. Regardless, no interruption in flowrate monitoring is required even in the event of fluid phase change.

Embodiments described hereinabove include vortex flowmeter measurements that are enhanced to account for periods where vortex frequency measurements may be compromised due to the emergence of a fluid phase change. Thus, as a practical matter, the advantages of improved accuracy and range from direct measurements may be retained. More specifically, even where perturbations emerge as a result of multi-phase flowing fluid, as is common for an oilfield well, the ability of the flowmeter to detect transit time of perturbations allows for continued accurate flowrate detection.

The preceding description has been presented with reference to presently preferred embodiments. However, other embodiments not detailed hereinabove may be employed. For example, the flowmeter utilized may be of a fluidic oscillator type, directed at lower flowrate monitoring, perhaps even outside of the oilfield environment. Furthermore, persons skilled in the art and technology to which these embodiments pertain will appreciate that still other alterations and changes in the described structures and methods of operation may be practiced without meaningfully departing from the principle and scope of these embodiments. Furthermore, the foregoing description should not be read as pertaining only to the precise structures described and shown in the accompanying drawings, but rather should be read as consistent with and as support for the following claims, which are to have their fullest and fairest scope.

The invention claimed is:

1. A method of detecting flowrate of a fluid in a well with a multiphase flowmeter, the method comprising:

flowing a flow of fluid through a channel of the flowmeter, wherein a bluff body disposed therein forms shedded vortices during a period of consistent phase of the fluid;

detecting a frequency of the vortices to ascertain flowrate of the fluid during the consistent phase period;

forming a perturbation by introduction of the bluff body to the flow of fluid during a period of transitioning phase of the fluid; and detecting the perturbation at multiple locations in the channel separated by a known distance for calculating a flowrate for the flow of fluid during the transitioning phase based on a time difference between the detections of the perturbation.

2. The method of claim 1 wherein the locations in the channel are downstream of the bluff body.

3. The method of claim 1 wherein the detecting of the frequency of the vortices is achieved with a sensor adjacent the bluff body.

4. The method of claim 3 wherein the detecting of the perturbation is at the location of the sensor adjacent the bluff body and at a location downstream thereof.

5. The method of claim 1 wherein the detecting of the perturbation is achieved with a sensor that is one of a temperature sensor, a pressure sensor, a piezo patch sensor and an acoustic sensor.

6. The method of claim 5 wherein the detecting of the perturbation with the acoustic sensor comprises:

transmitting an acoustic signal with a transmitter positioned at an opposite side of the channel from the acoustic sensor; and monitoring reception of the signal by the sensor as the perturbation flows through the channel.

7. The method of claim 5 wherein the piezo sensor is an encapsulated piezo patch lining a housing defining the channel with exposed portions at the multiple locations.

8. A method of detecting flowrate in a fluid channel, the method comprising:

introducing a bluff body to a flow of fluid in the channel to form one of a shedded vortex and a perturbation of the fluid;

detecting the one of the vortex and the perturbation at a first location in the channel;

detecting the one of the vortex and the perturbation at a second location in the channel downstream of the first location; and calculating a flowrate for the flow of fluid based on a time difference between the detections.

9. The method of claim 8 wherein the flow of fluid is a multiphase flow and the calculating of the flowrate is substantially continuous irrespective of fluid phase.

10. The method of claim 8 further comprising:

generating a frequency of vortices from the flow of fluid with the bluff body during a period of a consistent phase of the fluid; and detecting the frequency of vortices at the bluff body to ascertain the flowrate in advance of the calculating of the flowrate based on the time difference between the detections.

11. The method of claim 10 further comprising generating the perturbation from the flow of fluid with the bluff body during a period of transitioning phase of the fluid to support the calculating of the flowrate in absence of the detecting of the frequency of the vortices.

12. A multiphase flowmeter comprising:

a housing to define a channel to accommodate a flow of fluid there-through;

a bluff body secured within the channel to form one of a vortex and a perturbation during the flow of fluid through the channel;

a first sensor for detection of the one of the vortex and the perturbation, the first sensor at a first location that is one of at the bluff body and downstream of the bluff body; and a second sensor for detection of the one of the vortex and the perturbation, the second sensor at a second location that is at a known distance downstream of the first sensor to provide time of flight information between the detections for ascertaining flowrate of the flow of fluid.

13. The multiphase flowmeter of claim 12 wherein the fluid is an oilfield fluid and the flowmeter is configured for incorporation into a permanent downhole installation in a well.

14. The multiphase flowmeter of claim 12 wherein the fluid is an oilfield fluid and the flowmeter is configured for incorporation into a logging tool.

15. The multiphase flowmeter of claim 12 wherein the flowmeter is configured as a fluidic oscillator.

16. The multiphase flowmeter of claim 12 wherein the sensors are selected from a group consisting of a temperature sensor, a pressure sensor, an acoustic sensor, and a piezo sensor.

17. The multiphase flowmeter of claim 16 wherein the piezo sensor is an encapsulated piezo patch lining an interior of the housing with an exposed first portion at a first zone to serve as the first sensor and an exposed second portion at a second zone to serve as the second sensor.

18. The multiphase flowmeter of claim 16 wherein the sensors are acoustic sensors, the flowmeter further comprising acoustic transmitters at locations opposite the acoustic sensors within the housing for transmitting acoustic signals to the acoustic sensors for the detections thereat.

19. The multiphase flowmeter of claim 12 wherein the first sensor is a first supplemental sensor downstream of the bluff body and the second sensor is a second supplemental sensor downstream of the first supplemental sensor, the supplemental sensors for detecting the perturbation during a period of transitioning phase of the fluid, the flowmeter further comprising a bluff body sensor at the bluff body for detecting a frequency of shedded vortices during a period of consistent phase of the fluid.

20. The multiphase flowmeter of claim 19 wherein bluff body sensor is a pressure sensor and the supplemental sensors are of a piezo patch variety.

* * * * *